US009156012B2

(12) United States Patent
Mann et al.

(10) Patent No.: US 9,156,012 B2
(45) Date of Patent: Oct. 13, 2015

(54) METHOD AND DEVICE FOR MIXING SAMPLES ON A SUPPORT

(75) Inventors: Karl-Heinz Mann, Weilheim (DE); Thomas Mayer, Garmisch-Partenkirchen (DE); Friedhelm Vieth, Wielenbach (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 1157 days.

(21) Appl. No.: 12/015,000

(22) Filed: Jan. 16, 2008

(65) Prior Publication Data
US 2008/0113450 A1  May 15, 2008

Related U.S. Application Data

(62) Division of application No. 11/146,343, filed on Jun. 6, 2005, now abandoned.

(30) Foreign Application Priority Data

Jun. 11, 2004  (DE) .......................... 10 2004 028 303

(51) Int. Cl.
*B01F 13/02* (2006.01)
*B01F 13/00* (2006.01)
(Continued)

(52) U.S. Cl.
CPC ......... *B01F 13/0272* (2013.01); *B01F 13/0059* (2013.01); *B01F 2215/0037* (2013.01); *B01J 2219/00493* (2013.01);
(Continued)

(58) Field of Classification Search
CPC .............. G01N 1/37; G01N 2001/387; G01N 2035/00524; G01N 2035/00534; G01N 2035/1058; G01N 2035/106; B01F 13/02

USPC .................................................. 366/101–107
See application file for complete search history.

(56) References Cited

U.S. PATENT DOCUMENTS 3,398,935 A * 8/1968 Livesey et al. ................ 366/101
3,854,703 A   12/1974 Gibbs et al.
(Continued)

FOREIGN PATENT DOCUMENTS

EP  0281958  9/1988
EP  0643989  3/1995
(Continued)

OTHER PUBLICATIONS

Beer, S. et al., "Impaired microvascular function is associated with raised plasma N-terminal pro-brain natriuretic peptide level in Type 2 diabetic patients," Diabetologia, vol. 46, Supplement 2, Aug. 2003, p. A414-A415.
(Continued)

*Primary Examiner* — Melanie Y Brown
*Assistant Examiner* — Rebecca Martinez
(74) *Attorney, Agent, or Firm* — Barnes & Thornburg LLP

(57) ABSTRACT

A method for detecting analytes in a liquid is provided in which the liquid is subjected to a mixing treatment on an area of a support which has in particular immobilized reactants, wherein in the mixing treatment the liquid is impinged upon by a stream of gas that sweeps across at least some areas of the support surface in a scanning manner by means of a jet directed towards the support surface. The invention also concerns a method for mixing a liquid sample comprising an analyte and a device for carrying out the method.

19 Claims, 1 Drawing Sheet

(51) Int. Cl.
  *B01L 3/00* (2006.01)
  *G01N 35/00* (2006.01)
(52) U.S. Cl.
  CPC .......... *B01J 2219/00511* (2013.01); *B01J 2219/00605* (2013.01); *B01L 3/508* (2013.01); *G01N 2035/00544* (2013.01); *Y10T 436/25* (2015.01)

(56) References Cited

U.S. PATENT DOCUMENTS

| | | | |
|---|---|---|---|
| 3,876,380 A * | 4/1975 | Helriegel | 422/102 |
| 4,479,720 A | 10/1984 | Mochida et al. | |
| 4,664,526 A * | 5/1987 | Scheffler et al. | 366/106 |
| 4,774,055 A | 9/1988 | Wakatake et al. | |
| 4,815,978 A | 3/1989 | Mazza et al. | |
| 5,009,998 A | 4/1991 | Chow et al. | |
| 5,362,147 A * | 11/1994 | Schels et al. | 366/107 |
| 5,489,154 A | 2/1996 | Algreen-Ussing | |
| 5,650,327 A | 7/1997 | Copeland et al. | |
| 5,780,306 A | 7/1998 | Schels et al. | |
| 5,897,837 A | 4/1999 | Mizuno | |
| 6,063,564 A | 5/2000 | Ishikawa et al. | |
| 6,180,417 B1 * | 1/2001 | Hajizadeh et al. | 436/518 |
| 6,485,918 B1 | 11/2002 | Schemer et al. | |
| 6,656,685 B2 | 12/2003 | Utermohien et al. | |
| 6,881,579 B2 | 4/2005 | Hilson et al. | |
| 2002/0005725 A1 | 1/2002 | Scott | |
| 2002/0102554 A1 | 8/2002 | Uterhohlen et al. | |
| 2002/0182603 A1 | 12/2002 | Chapman et al. | |
| 2003/0022176 A1 | 1/2003 | Schremp et al. | |
| 2003/0219890 A1 | 11/2003 | Gordon et al. | |
| 2004/0106134 A1 * | 6/2004 | Economides et al. | 435/6 |

FOREIGN PATENT DOCUMENTS

| | | |
|---|---|---|
| EP | 1530047 | 5/2005 |
| JP | 52-104185 | 9/1977 |
| TW | 270898 | 2/1996 |
| WO | WO 00/10011 | 2/2000 |
| WO | WO 01/22086 | 3/2001 |
| WO | WO 02/089657 | 11/2002 |
| WO | WO 03/040691 | 5/2003 |
| WO | WO 2004/046722 | 6/2004 |

OTHER PUBLICATIONS

Epshteyn, V. et al., "Utility of B-Type Natriuretic Peptide (BNP) as a Screen for Left Ventricular Dysfunction in Patients with Diabetes," Diabetes Care, vol. 26, No. 7, Jul. 2003, p. 2081-2087.

McDonagh, T. et al., "Biochemical detection of left-ventricular systolic dysfunction," The Lancet, vol. 351, Jan. 3, 1998, p. 9-13.

Siebenhofer, A. et al., "Plasma N-terminal pro-brain natriuretic peptide in Type 1 diabetic patients with and without diabetic nephropathy," Diabetes UK, Diabetic Medicine, 20, 535-539 (2003).

Yngen, M. et al., "Enhanced P-selection expression and increased soluble CD40 Ligand in patients with Type 1 diabetes mellitus and microangiopathy: evidence for platelet hyperactivity and chronic inflammation," Diabetologia (2004) 47:537-540.

* cited by examiner

METHOD AND DEVICE FOR MIXING SAMPLES ON A SUPPORT

RELATED APPLICATIONS

This application is a divisional of U.S. patent application Ser. No. 11/146,343, filed Jun. 6, 2005, which claims priority to German Patent Application No. 102004028303.6 filed Jun. 11, 2004.

FIELD OF THE INVENTION

The invention concerns a method for detecting analytes in a liquid in which the liquid is subjected to a mixing treatment on an area of a support preferably of a biochip which in particular has immobilized reactants.

BACKGROUND

The invention especially concerns methods for improving the mixing treatment of a liquid and in this connection methods for improving the way in which analytes in the liquid are brought to reactants that are immobilized on an area of the support and in particular of the biochip that is occupied by the liquid.

The following problem occurs in biochip applications and especially in immunoassay applications in which binding reactions are detected between reactants that are immobilized on a support surface and analytes that are present in a liquid that wets the support surface. The binding of analytes to immobilized reactants lowers the concentration of analytes in the liquid in a boundary layer on the support surface resulting in a depletion of analytes in the sample liquid in a boundary layer. Due to the usually low analyte diffusion rate which is normally only a few μm/s or less, new analyte molecules are not resupplied rapidly enough from the sample liquid volume so that long incubation times are required for immunological tests or such like to achieve an adequate measuring effect. There are various approaches for solving this problem in the prior art.

A mixing process is described in U.S. Pat. No. 6,485,918 for a microarray biochip with a deformable cover which is placed over the surface of the microarray. Deformation of the cover generates a flow movement in the liquid between the cover and microarray surface. Although this known method is suitable for flat biochips having a reactant immobilized on the bottom, it has the disadvantage that the cover must always be in contact with the sample liquid during the mixing process. Additional processing steps such as washing steps, reagent addition etc. may necessitate an opening of the cover with the associated risk of losing sample liquid and contamination.

A method and device for mixing samples near the interface in biosensor systems, namely biochips is known from WO 00/10011. In order to increase the sensitivity the liquid in the biochip is excited in this known method by mechanical waves (sound, ultrasound or surface waves) which is intended to improve mixing of the sample liquid especially at the chip/liquid boundary layer in order to enhance the diffusion of the analyte.

A device for controlling the temperature and mixing the contents of vessels of a microtitration plate for immunological tests is known from EP 0 281 958 A2. This known device comprises a cover which defines a hollow space into which a gas line discharges. A boundary wall of the cover that faces the titration plate is provided with gas outlet openings which are arranged eccentrically relative to the vessel axes of the individual vessels of the microtitration plate and are aligned at an angle to the surfaces of the liquids in the individual vessels. Temperature control and generation of a rotary mixing movement of the liquid in the individual vessels is achieved by blowing in warm air through the gas outlet openings.

U.S. Pat. No. 6,063,564, U.S. Pat. No. 4,479,720 and U.S. Pat. No. 5,009,998 for example also concern the improved mixing of sample liquids in sample tubes as liquid containers.

The mechanical mixing processes known from the prior art such as shaking, application of ultrasound, vortexing etc. have proven to be not particularly effective and advantageous for biochips with a flat support or planar support surface with an array of reactants.

SUMMARY OF THE INVENTION

The present invention relates to a method for mixing a liquid sample comprising an analyte, the method comprising providing a support comprising an area comprising a reactant immobilized thereon and the sample, wherein the sample wets the area, and providing a stream of gas that impinges upon and sweeps across at least a part of the area in a scanning manner, the stream of gas being provided by means of a jet directed toward the area, thereby causing a mixing of the liquid sample and thereby causing the analyte to be available for reaction with the immobilized reactant.

The invention further relates to a method for detecting an analyte in a liquid sample comprising providing a support comprising an area comprising a reactant immobilized thereon and the sample, wherein the sample wets the area, providing a stream of gas that impinges upon and sweeps across at least a part of the area in a scanning manner, the stream of gas being provided by means of a jet directed toward the area, thereby causing a mixing of the liquid sample and thereby causing the analyte to be available for binding with the immobilized reactant, and detecting the binding of the analyte with the immobilized reactant.

The invention further relates to a device for detecting an analyte in a liquid sample, the device comprising a holder, a support held by the holder and comprising an area comprising a reactant immobilized thereon, the support containing the liquid sample which wets the area, a gas supply device comprising a jet for supplying a stream of gas to the area, and a drive device for generating relative movement between the jet and the holder whereby the stream of gas sweeps across at least a part of the area in a scanning manner, thereby mixing the sample and causing the analyte to be available for reaction with the immobilized reactant.

BRIEF DESCRIPTION OF THE DRAWINGS

The invention is further elucidated in the following with reference to the figures.

DESCRIPTION OF THE INVENTION

Figure 1:
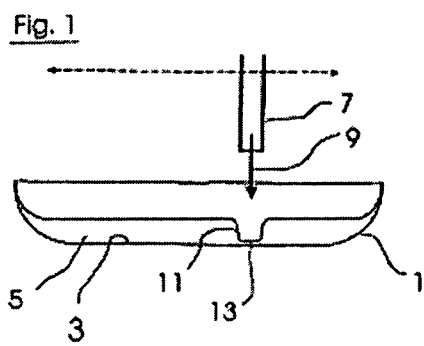
FIG. 1 shows a greatly simplified schematic representation of a diagrammatic sketch to illustrate the method comprising a trough-shaped biochip and a gas jet that can be moved above it and FIG. 2 shows a greatly simplified schematic representation of a device according to the invention.

The object of the invention is to propose a method of the type stated above which increases the measuring sensitivity or reduces the incubation time required to achieve an adequate measuring effect when performing tests based on binding reactions between analytes in a sample liquid and reactants on a support wetted by the sample liquid and thus for typical biochip applications. Furthermore, the binding reaction between analytes and reactants should occur homogeneously and independently of the location over the entire chip. This means that reactants that are in the middle or at the edge of the support or microarray chip can bind the analyte essentially at the same rate and efficiency.

In order to achieve this object in the case of the aforementioned method for detecting analytes in a liquid the invention proposes that the liquid is impinged upon by a stream of gas that sweeps across at least some areas in a scanning manner by means of a jet directed towards the support surface during the mixing treatment.

This process which is extremely suitable especially when using trough-shaped biochips having an essentially flat bottom as the support surface results in an efficient local mixing of the sample liquid containing the analytes in the area of the zone that is currently being impinged upon by the gas stream. It is expedient to direct the jet from above onto the sample liquid in such a manner that the gas stream locally displaces sample liquid in its impact area. As a result the level of sample liquid in the impact area of the gas stream is reduced to a very low value of for example only a few µm and the sample liquid is efficiently homogenized by vortexing in a zone encompassing this area with the reduced liquid level. Since the impact point of the gas stream sweeps across the support surface in a scanning manner the zone where the sample liquid is intensively mixed on the bottom of the chip migrates across the support surface such that new analytes are supplied in an accelerated manner to the boundary layer that is initially depleted of analyte due to prior binding reactions. This increases the probability of further binding reactions between the analytes and the immobilized reactants which can thus increase the sensitivity or reduce the incubation period and improve the homogeneity and especially the position-independent homogeneity of analyte binding compared to conventional methods.

The stream of gas is preferably an air stream in particular a stream of humidified air. The air humidification prevents the biochip from drying.

The gas stream can also alternatively be a stream of inert gas.

A relative movement is generated between the jet and the support in order to sweep the area with the gas stream in a scanning manner. It can be swept several times and in particular periodically. This can for example be achieved by moving the jet in a predetermined manner while holding the support or by moving the support while holding the jet. This also does not exclude the possibility of moving the jet as well as the support in order to impinge the sample liquid in a scanning manner.

As a vessel for the sample liquid it is preferable to use a trough-shaped vessel in particular having an essentially flat bottom as the support surface for the immobilized reactants. In particular a biochip with an array of individual surface areas on which the reactants are located is suitable as a support.

Alternatively a trough-shaped vessel can be used as a sample vessel which contains separate support elements such as solid phase microparticles for the immobilized reactants.

A continuous, essentially uniform stream of air is preferably used as an air stream to impinge on the liquid. However, this does not exclude the possibility that in alternative embodiments a modulated and in particular a pulsing stream of air is used.

A particular advantage of the invention is that the proposed mixing treatment of the liquid enables a good homogeneity of the binding reaction between analytes and immobilized reactants independent of the position over the entire support surface.

Another subject matter of the invention is a device for carrying out the method, the device being characterized by a holder for holding at least one support in particular a biochip which has a bottom surface with reactants immobilized thereon or optionally a bottom surface for depositing support elements with reactants immobilized thereon, a gas supply device comprising at least one jet for ejecting a gas stream towards the bottom surface of a support located in the holder and a drive device for generating a relative movement between the jet and the holder such that a stream of gas discharged from the jet sweeps across at least some areas of the bottom surface in a scanning manner.

According to a further development of the invention the holder is movably mounted and the drive device is designed to move the holder relative to the jet.

In an alternative embodiment of the invention the jet is movably mounted and the drive device is designed to move the jet relative to the holder.

According to a further development of the invention the gas supply device is designed to generate a jet of air that is discharged by means of the jet.

The gas supply device advantageously comprises an air moistening device.

Especially when carrying out mass tests it is proposed that the holder is designed to hold a plurality of supports or sample vessels and that each support or sample vessel is allocated at least one jet.

By varying the arrangement of jets, the jet geometry, the relative jet movement and the intensity of the stream of air, the system according to the invention can be readily adapted to biochips that can be designed relatively freely having a flat analyte reservoir and a flat bottom. A plurality of biochips can be easily processed in parallel since a pressure reservoir can simultaneously supply many jets in a defined manner.

FIG. 1 shows a trough-shaped biochip 1 having an essentially flat trough bottom 3 on which reactants or capture molecules are immobilized preferably in a microarray arrangement. The bottom surface 3 is wetted by a sample liquid 5 which contains analytes that can bind with reactants on the bottom 3 of the biochip 1 where for example this binding can be detected by measuring the fluorescence.

Since after adding the sample fluid 5 to the biochip 1 a zone of depleted free analyte in the liquid soon forms in a boundary layer near to the bottom 3 due to binding processes, there is normally a delay in further binding. In order to avoid this disadvantageous retarding effect, a gas jet 7 is moved according to FIG. 1 over the surface of the sample liquid 5 such that the point of impact of the gas stream 9 on the liquid surface sweeps across the support area 3 while maintaining an intermediate layer of liquid 5. As indicated at 11 in FIG. 1, the liquid 5 is displaced in the area of the respective impact point of the gas stream 9. Only a very thin film of sample liquid 13 remains in the area of this zone 11. However, as a result of the gas stream 9 impinging on the liquid, the liquid in the area of the film 13 is well mixed such that the "analyte depletion zone" is locally broken through at this position and new analytes are available for binding to the reactants. Since the zone 11 can be guided over the entire area of the bottom 3 that is of interest, it is possible to distribute the increased supply of analyte uniformly over this surface area 3. Hence the method according to the invention increases the efficiency of bindings per unit of time which is associated with a reduction of the required incubation time to achieve an adequate measuring effect such as in immunoassay applications.

Figure 2:
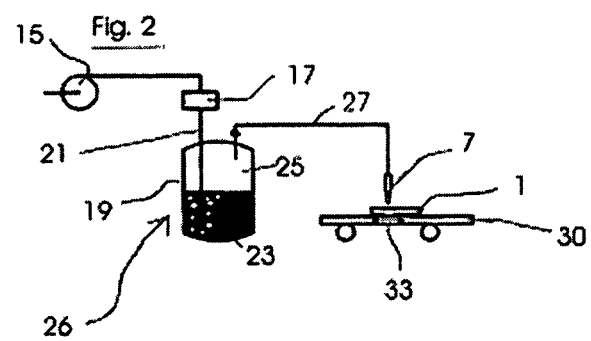

FIG. 2 shows a greatly simplified schematic structure of a device according to the invention comprising an air pump 15 which is for example designed as a membrane pump to generate an air current. An air flow sensor 17 connected to the pressure side of the pump 15 is used to monitor the air current and thus serves as an actual value transmitter to regulate the air current. In test measurements an air current of about 7 ml/s has proven to be advantageous.

In order to reduce evaporation of sample liquid in the biochip 1, the air supplied to the jet 7 is moistened by an air moistening device 26. In the example shown in FIG. 2 a pressure vessel 19 partially filled with water is used for this purpose. The air conveyed by the pump 15 is blown into the water reservoir 23 through the line 21. The pressurized air with an increased moisture content which then rises above the water reservoir 23 in the container volume 25 then reaches jet 7 via the line 27. The moistened air is then blown onto the biochip 1 in the stream from the jet 7 in order to achieve the effect elucidated in connection with FIG. 1.

In FIG. 2 the biochip 1 is on a holder 30 which can for example be a carriage moved by a motor. The holder 30 can be moved in such a manner that the stream of air directed towards the bottom of the biochip through the fixed jet 7 can scan the support area of the biochip 1 that is occupied with immobilized reactants. In this connection it can be designed such that the holder 30 can execute horizontal backward and forward motions indicated by the double arrow 33 and also a reciprocating motion at right angles thereto.

It should be noted that, depending on needs, jets 7 having gas outlet slits of different shapes can be used. Thus it is not excluded that one jet has an elongate outlet slit which for example approximately overlaps the complete width of a biochip 1. The sequence of movements when the biochip is moved relative to the jet 7 can then be reduced to a simple forwards and backwards motion. In the example of FIGS. 1 and 2 the gas stream 9 impacts the liquid approximately vertically. Alternatively it can also be provided within the scope of the invention that the gas stream strikes the liquid at a tilted angle relative to the vertical.

It is also possible to use jets having several exit slits or capillaries. Thus in tests on the device a jet comprising two parallel steel capillaries was used that were spaced 1.4 mm apart and which each had an inner diameter of 0.5 mm. The capillary length is 10 mm. The distance between the jet opening and the sample fluid surface was ca. 2 mm in the tests. The filling level of the sample liquid in the biochip was ca. 1 mm. The analyte-sensitive zone of the biochip had an area of about $2.5 \times 6$ mm$^2$. A stepping motor drive was used for the reciprocating movement of the biochip under the jet at a frequency of about 0.5 Hz.

What is claimed is:

1. A method for mixing a liquid sample comprising an analyte, the method comprising:
   (i) providing a sample vessel comprising side walls and a bottom area, said sample vessel containing a reactant and the sample,
   (ii) providing a stream of gas directed from above that impinges upon the liquid sample by means of a jet vertically directed toward the bottom area to locally displace sample liquid at the point of impact of said stream of gas, and
   (iii) generating relative movement between the jet and the vessel during step (ii), so that the point of impact of said stream of gas sweeps across the entire bottom area in a scanning manner, thereby causing a mixing of the liquid sample.

2. The method of claim 1, wherein the reactant is immobilized on the bottom area.

3. The method of claim 1, wherein the bottom area is essentially flat.

4. The method of claim 1, wherein the stream of gas is a stream of moistened air.

5. The method of claim 1, wherein the bottom area comprises a biochip having multiple areas upon which a reactant is immobilized, and said point of impact from said stream of gas sweeps across the entire biochip area.

6. The method of claim 1, wherein the stream of gas is continuous and essentially uniform.

7. A method for improved mixing for reactions involving reactions between reactants immobilized on a support surface and analytes present in a liquid sample, wherein a liquid boundary layer of depleted analytes is formed on the immobilized reactants, the method comprising:
   (i) providing a support comprising an area, wherein said area comprises said immobilized reactant, and said liquid sample comprising said analytes, wherein the liquid sample wets the area,
   (ii) providing a stream of gas projected from a jet positioned above the liquid sample wherein the point of impact from said stream of gas impinges upon the surface of the liquid sample, locally displacing sample liquid at the point of impact, and
   (iii) generating relative movement between the jet and the support during step (ii) so that the point of impact from said stream of gas is swept in a scanning manner across the entire area comprising the reactant, thereby providing a mixing of the liquid sample and causing the analyte to be available for reaction with the immobilized reactant.

8. The method of claim 7, wherein the stream of gas is a stream of moistened air.

9. The method of claim 7, wherein the support is a trough-shaped vessel having an essentially flat bottom.

10. The method of claim 9, wherein the vessel also contains microparticles with a reactant immobilized thereon.

11. The method of claim 7, wherein the support comprises a biochip having multiple areas upon which a reactant is immobilized.

12. The method of claim 7, wherein the stream of gas is continuous and essentially uniform.

13. A method for detecting an analyte in a liquid sample comprising:
   (i) providing a support comprising an area, wherein said area comprises a reactant immobilized thereon, and said liquid sample wets the area,
   (ii) providing a stream of gas projected from a jet positioned above the sample wherein the point of impact from said stream of gas impinges upon the surface of said sample, wherein the level of sample liquid in the impact area of the stream of gas is reduced to only a few micrometers, and
   (iii) generating relative movement between the jet and the support during step (ii) so that the point of impact from said stream of gas migrates across the entire area comprising the reactant, thereby providing a mixing of the liquid sample and causing the analyte to be available for reaction with the immobilized reactant, and
   detecting the binding of the analyte with the immobilized reactant.

14. The method of claim 13, wherein the stream of gas is a stream of moistened air.

15. The method of claim 13, wherein the support is a trough-shaped vessel having an essentially flat bottom, said vessel comprising microparticles with a reactant immobilized thereon.

16. The method of claim 13, wherein the support comprises a biochip having multiple areas upon which a reactant is immobilized.

17. The method of claim 1 wherein the point of impact of said stream of gas is swept across the bottom area of the sample vessel multiple times.

18. The method of claim 7 wherein the point of impact of said stream of gas is swept across the sample multiple times.

19. The method of claim 7 wherein the level of sample liquid in the impact area of the stream of gas is reduced to only a few micrometers.

\* \* \* \* \*